United States Patent [19]
Pinski

[11] Patent Number: 5,612,348
[45] Date of Patent: Mar. 18, 1997

[54] METHOD OF TREATING WARTS

[76] Inventor: James B. Pinski, 55 E. Washington St., Suite 3404, Chicago, Ill. 60602

[21] Appl. No.: 849,764

[22] Filed: Mar. 12, 1992

[51] Int. Cl.⁶ ..................................................... A61K 31/52
[52] U.S. Cl. ............................................................. 514/262
[58] Field of Search ............................................. 514/262

[56] References Cited

U.S. PATENT DOCUMENTS 4,199,574  4/1980  Schaeffer ................................. 514/262

OTHER PUBLICATIONS

Andrewes, Viruses of Vertebrates, 1964, The Williams and Wilkins Co. Balto., Md, pp. 199–200.

Primary Examiner—Jerome D. Goldberg
Attorney, Agent, or Firm—James Ray & Associates

[57] ABSTRACT

A method of treating a viral infection in a human manifested as at least one of warts, carcinomas, cancer of the cervix, *Bowenoid papulosis* and epidermal dysplasia verruciformis is disclosed. This method comprises the step of administering an effective amount of a substituted purine of formula (I).

8 Claims, No Drawings

METHOD OF TREATING WARTS

FIELD OF THE INVENTION

The present invention relates, in general, to substituted purine compounds and their pharmaceutically acceptable salts and, more particularly, this invention relates to a method of treating warts, premalignancies, carcinomas, cancer of the cervix, human papilloma virus, *Bowenoid papulosis* and epidermal dysplasia verruciformis with such substituted purine compounds.

BACKGROUND OF THE INVENTION

Prior to the present invention substituted purine compounds used in the method of the present invention have been taught in U.S. Pat. No. 4,199,574. The teachings of this reference are incorporated herein by reference thereto.

The compounds disclosed were reported to have antiviral activity against various classes of DNA and RNA viruses both in in vitro and in vivo experiments. In particular, the compounds were found to be active as anti-virals against cytomegalovirus, adenovirus, especially adenovirus 5, rhino virus, Mengo virus and Sindbis virus. They are also especially active as an antiviral against vaccinia, and herpes viruses, including simplex, zoster and varicella, in mammals, which cause such diseases as, for example, herpetic keratitis in rabbits and herpetic encephalitis in mice.

As used in this reference the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops etc., depending on whether the preparation is used to treat internal or external viral infections.

For internal infections the compositions are administered orally or parenterally at dose levels, calculated as the free base, of about 0.1 to 250 mg per kg, preferably 1.0 to 50 mg per kg, of mammal body weight, and are used in man in a unit dosage form, administered a few times daily in the amount of 1 to 250 mg per unit dose.

For oral administration, fine powders or granules many contain diluting, dispersing and/or surface active agents, and may be presented in a draught, in water or in a syrup; in capsules or sacnets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10%, more preferably, 0.1 to 7%, most preferably 0.2% w/v. The solution may contain antioxidants, buffers, etc.

Alternatively for infections of the eye, or other external tissues e.g. mouth and skin the compositions are preferably applied to the infected part of the body of the patient as a topical ointment or cream. The compounds may be presented in an ointment, for instance, with a water soluble ointment base, or in a cream, for instance, with an oil in water cream base, in a concentration of from about 0.1 to 10%; preferably 0.1 to 7%, most preferably 1% w/v.

SUMMARY OF THE INVENTION

The present invention provides a method of treating a viral infection manifested in a human as at least one of warts, premalignancies, carcinomas, cancer of the cervix, human papilloma virus, *Bowenoid papulosis* and epidermal dysplasia verruciformis. This method comprises the step of administering a dosage of between about 1,500 mg/day and about 15,000 mg/day of a substituted purine of formula (I)

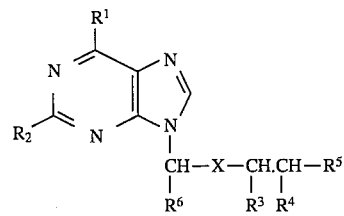

wherein X is one of sulphur and oxygen; $R^1$ is hydroxy, $R^2$ is amino; $R^3$ is selected from the group consisting of hydrogen, straight or branched chain or cyclic alkyl, hydroxyalkyl, benzyloxyalkyl and phenyl; $R^4$ is selected from the group consisting of hydrogen, hydroxy, and lower alkyl; $R^5$ is selected from the group consisting of hydrogen, hydroxy, amino, alkyl, hydroxyalkyl, benzoyloxy, benzoyloxyalkyl, benzyloxy, sulphamoyloxy, phosphate, carboxypropionyloxy, and acetoxy; $R^6$ is selected from the group consisting of hydrogen, alkyl, hydroxyalkyl and a pharmaceutically acceptable salt thereof.

OBJECTS OF THE INVENTION

It is, therefore, one of the primary objects of the present invention to provide a method of treating a viral infection manifested in a human as at least one of warts, premalignancies, carcinomas, cancer of the cervix, human papilloma virus, *Bowenoid papulosis* and epidermal dysplasia verruciformis.

Another object of the present invention is to provide a method of treating a viral infection with a medication which will have substantially no adverse side effects when administered within the prescribed dosages.

Still another object of the present invention is to provide a method of treating a viral infection in which the medications can be administered to humans in a variety of forms.

In addition to the above described objects and advantages of the present invention, various other objects and advantages of the method of treating a viral infection will become more readily apparent to those persons who are skilled in the medical art from the following more detailed description of the invention.

BRIEF DESCRIPTION OF PRESENTLY PREFERRED AND ALTERNATIVE EMBODIMENTS OF THE INVENTION

The instant invention is predicated on the discovery that a substituted purine of formula (I) is effective as a method of treating a viral infection. As used in the description of the instant invention, the term "viral infection" means an infection manifested in a human as at least one of warts, premalignancies, carcinomas, cancer of the cervix, human papilloma virus, Bowenoid papulosis and epidermal dysplasia verruciformis. This discovery was made while treating a patient with the substituted purine of formula (I) for an unrelated infection.

The method of treating a viral infection, according to the present invention, comprises the step of administering an effective dosage, preferably, of between about 1,500 mg/day and about 15,000 mg/day of a substituted purine of formula (I)

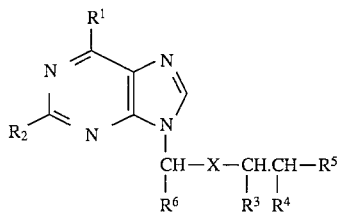

wherein X is selected from the group consisting of sulphur and oxygen $R^1$, in this formula, is hydroxy. $R^2$ is amino. $R^3$ is selected from the group consisting of hydrogen, straight chain alkyl, branched chain alkyl, cyclic alkyl, hydroxalkyl, benzyloxyalkyl and phenyl. $R^4$ is selected from the group consisting of hydrogen, hydroxy, and lower alkyl. $R^5$ is selected from the group consisting of hydrogen, hydroxy, amino, alkyl, hydroxyalkyl, benzoyloxy, benzoyloxyalkyl, benzyloxy, sulphamoyloxy, phosphate, carboxypropionyloxy, and acetoxy. $R^6$ is selected from the group consisting of hydrogen, alkyl, hydroxyalkyl and a pharmaceutically acceptable salt thereof.

A more preferred dosage will be in a range of between about 2,500 mg/day and about 10,000 mg/day. In most cases, the most preferred dosage will be in a range of between about 5,000 mg/day and about 10,000 mg/day.

In one presently preferred substituted purine of formula (I), used in the treatment method, $R^1$ is hydroxy $R^2$ is amino. $R^3$ is selected from the group consisting of hydrogen, straight chain alkyl, branched chain alkyl, cyclic alkyl, hydroxalkyl, benzyloxyalkyl and phenyl. $R^4$ is selected from the group consisting of hydrogen, hydroxy, and lower alkyl. $R^5$ is selected from the group consisting of hydrogen, hydroxy, amino, alkyl, hydroxyalkyl, benzoyloxy, benzoyloxyalkyl, benzyloxy, sulphamoyloxy, phosphate, carboxypropionyloxy, and acetoxy. $R^6$ is selected from the group consisting of hydrogen, alkyl, hydroxyalkyl and a pharmaceutically acceptable salt thereof.

In a still more preferred embodiment of the substituted purine of formula (I), $R^1$ is hydroxy $R^2$ is amino. $R^5$ is selected from the group consisting of hydroxy, benzoyloxy, and $R^3$, $R^4$ and $R^6$ are one of all hydrogen atoms and a pharmaceutically acceptable slat thereof.

Even, more preferably, $R^1$ is hydroxy; $R^2$ is amino; $R^3$ is selected from the group consisting of hydrogen, straight chain alkyl, branched chain alkyl, cyclic alkyl, hydroxyalkyl and phenyl; $R^4$ is one of hydrogen and hydroxy; $R^5$ is selected from the group consisting of hydrogen, hydroxy, hydroxyalkyl, amino, carboxypropionyloxy, acetoxy, benzyloxy, benzoyloxy, benzoyloxyalkl, phosphate, and sulphamolyloxy; $R^6$ is selected from the group consisting of hydrogen, alkyl, and hydroxyalkyl; and a pharmaceutically acceptable salt thereof in the substituted purine of formula (I).

In a more limited embodiment, the present invention provides a method of treating a viral infection manifested in a human as at least one of warts, premalignancies, carcinomas, cancer of the cervix, human papilloma virus, *Bowenoid papulosis* and epidermal dysplasia verruciformis. According to this embodiment, the method comprises the step of administering, as a dosage, between about 1,500 mg/day and about 15,000 mg/day of a pharmaceutical composition of a substituted purine of the formula (I)

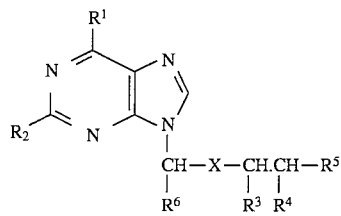

wherein X is selected from the group consisting of sulphur and oxygen; $R^1$ is hydroxy; $R^2$ is amino; $R^3$ is selected from the group consisting of hydrogen, straight chain, branched chain, cyclic alkyl, hydroxyalkyl, benzyloxyalkyl and phenyl; $R^4$ is selected from the group consisting of hydrogen, hydroxy, and lower alkyl; $R^5$ is selected from the group consisting of hydrogen, hydroxy, amino, alkyl, hydroxyalkyl, benzoyloxy, benzoyloxyalkyl, benzyloxy, sulphamoyloxy, phosphate, carboxypropionyloxy, and acetoxy; $R^6$ is selected from the group consisting of hydrogen, alkyl, hydroxyalkyl and a pharmaceutically acceptable salt thereof; together with a pharmaceutically acceptable carrier therefor.

In this alternative embodiment the substituted purine of formula (I) can be selected from the group consisting of:
9(2-benzolyloxyethoxymethyl)guanine;
9-(3-hydroxypropoxymethyl) guanine; and
9-{2-(3-carboxypropionyloxy)ethoxymethyl}guanine.

In still another alternative embodiment the substituted purine of formula (I) is selected from the group consisting of:
9-(3-Benzoylpropoxymethyl)guanine;
9-[1-(2-Hydroxyethoxy)ethyl]guanine; and
9-Ethoxymethylguanine.

In another alternative embodiment, the present invention provides a method of treating a viral infection manifested in a human as at least one of warts, premalignancies, carcinomas, cancer of the cervix, human papilloma virus, *Bowenoid papulosis* and epidermal dysplasia verruciformis, which comprises the step of administrating a dosage of between about 1,500 mg/day and 15,000 mg/day of 9-(2-Formyloxyethoxymethyl) guanine or a pharmaceutically acceptable salt thereof.

In this embodiment such 9-(2-Formyloxyethoxymethyl) guanine or a pharmaceutically acceptable salt thereof, further includes a pharmaceutical acceptable carrier therefor.

In any of the embodiments discussed above the medication can be produced in the form of a tablet with each tablet containing between about 200 mg/day and about 800 mg/day of the substituted purine of formula (I).

Although a number of presently preferred and alternative embodiments of the method of treating a viral infection manifested in a human as at least one of warts, premalignancies, carcinomas, cancer of the cervix, human papilloma virus, *Bowenoid papulosis* and epidermal dysplasia verruciformis have been described above, it should be obvious that various other modifications and adaptations of the present invention can be made without departing from the spirit and scope of the appended claims.

I claim:
1. A method of treating a viral infection manifested in a human a warts, said method comprising the step of admin- istering a dosage of between about 1,500 mg/day and about 15,000 mg/day of a substituted purine of formula (I)

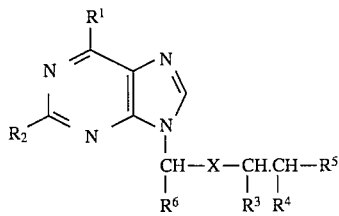

wherein x is oxygen; $R^1$ is hydroxy; $R^2$ is amino; $R^3$ is hydrogen; $R^4$ is hydrogen; $R^5$ is hydroxy; $R^6$ is hydrogen; and a pharmaceutically acceptable salt thereof.

2. A method of treating warts, according to claim 1, wherein said dosage is between about 2,500 mg/day and about 10,000 mg/day.

3. A method of treating warts, according to claim 2, wherein said dosage is between about 5,000 mg/day and about 10,000 mg/day.

4. A method of treating warts, according to claim 1, wherein said dosage is in the form of a tablet containing between about 200 mg/tablet and about 800 mg/tablet.

5. A method of treating a viral infection manifested in a human as warts, said method comprising the step of administering a dosage of between about 1,500 mg/day and about 15,000 mg/day of a substituted purine of formula (I)

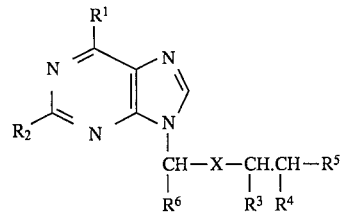

wherein x is oxygen; $R^1$ is hydroxy; $R^2$ is amino; $R^3$ is hydrogen; $R^4$ is hydrogen; $R^5$ is hydroxy; $R^6$ is hydrogen; and a pharmaceutically acceptable salt thereof; together with a pharmaceutically acceptable carrier therefor.

6. A method of treating warts, according to claim 5, wherein said dosage is administered in a tablet form and said purine of formula (I) is present in an amount of between about 200 mg/tablet and about 500 mg/tablet.

7. A method of treating warts, according to claim 5, wherein said dosage is between about 2,500 mg/day and about 10,000 mg/day.

8. A method of treating warts, according to claim 5, wherein said dosage is the form of a tablet containing between about 200 mg/tablet and about 800 mg/tablet.

* * * * *

UNITED STATES PATENT AND TRADEMARK OFFICE
CERTIFICATE OF CORRECTION

PATENT NO.  : 5,612,348
DATED       : March 18, 1997
INVENTOR(S) : James Bernard Pinski It is certified that error appears in the above-identified patent and that said Letters Patent is hereby corrected as shown below:

Column 3, line 22, after "oxygen", please insert --.--;

column 3, line 38, after "hydroxy", please insert --.--;

column 3, line 42, after "hydroxy", please delete ",";

column 3, line 50, after "hydroxy", please insert --.--;

column 3, line 53, please delete "slat" and insert --salt--;

column 3, line 60, after "phosphate", please delete ",";

column 3, line 62, after "alkyl", please delete ",".

Column 4, line 18, after "chain", please insert --alkyl--;

column 4, line 19, after "chain", please insert --alkyl--;

UNITED STATES PATENT AND TRADEMARK OFFICE
CERTIFICATE OF CORRECTION

PATENT NO. : 5,612,348
DATED : March 18, 1997
INVENTOR(S) : James Bernard Pinski It is certified that error appears in the above-identified patent and that said Letters Patent is hereby corrected as shown below:

column 4, line 24, after "carboxypropionyloxy", please delete ",";

column 4, line 30, after ":", please insert --9-(2-hydroxyethoxymethyl) guanine;--;

column 4, line 31, after "9", please insert -- - --;

column 4, line 34, after "embodiment", please insert --,--;

column 4, line 52, after "above", please insert --,--;

column 4, line 67, please delete "a" and insert --as--.

Signed and Sealed this

Fourteenth Day of March, 2000

Attest:

Attesting Officer

Q. TODD DICKINSON

Commissioner of Patents and Trademarks